United States Patent [19]

Hovis et al.

[11] Patent Number: 5,759,937
[45] Date of Patent: Jun. 2, 1998

[54] METHOD FOR REGENERATION OF A HYDROGEN FLUORIDE ALKYLATION CATALYST CONTAINING SULFONE, WATER, AND ASO

[75] Inventors: Keith W. Hovis; Richard L. Anderson, both of Bartlesville, Okla.

[73] Assignee: Phillips Petroleum Company, Bartlesville, Okla.

[21] Appl. No.: 724,745

[22] Filed: Oct. 2, 1996

Related U.S. Application Data

[60] Provisional application No. 60/014,121, Mar. 25, 1996.
[51] Int. Cl.$^6$ .................. B01J 20/34; C07C 2/62
[52] U.S. Cl. ............... 502/36; 502/35; 585/724; 585/802
[58] Field of Search ................ 502/34, 35, 36; 585/724, 802, 857

[56] References Cited

U.S. PATENT DOCUMENTS

| | | | |
|---|---|---|---|
| 5,347,065 | 9/1994 | Anderson | 585/724 |
| 5,386,076 | 1/1995 | Child et al. | 585/802 |
| 5,463,162 | 10/1995 | Eastman | 585/724 |

*Primary Examiner*—Michael Lewis
*Assistant Examiner*—Alexander G. Ghyka
*Attorney, Agent, or Firm*—Charles W. Stewart

[57] ABSTRACT

Disclosed is an alkylation process which utilizes a mixture of sulfone and hydrogen fluoride as an alkylation catalyst. The process provides for the removal of ASO and water from the alkylation catalyst that accumulates therein while minimizing the loss of sulfone and HF with the ASO and water removed.

6 Claims, 1 Drawing Sheet

5,759,937

METHOD FOR REGENERATION OF A HYDROGEN FLUORIDE ALKYLATION CATALYST CONTAINING SULFONE, WATER, AND ASO

This application claims the benefit of U.S. Provisional Application No. 60/014,121 filed Mar. 25, 1996.

The present invention relates to a hydrocarbon conversion process for the alkylation of olefin hydrocarbons by isoparaffin hydrocarbons which utilizes a catalyst mixture comprising a sulfone compound and a hydrogen halide compound. More specifically, the invention relates to a process for removing acid soluble oil and water from an alkylation catalyst used in an alkylation process system to prevent buildup therein.

BACKGROUND OF THE INVENTION

It has recently been discovered that a mixture, comprising a sulfone compound and a hydrogen halide compound, can be an effective catalyst for use in the alkylation of olefin hydrocarbons by isoparaffin hydrocarbons to produce an alkylate reaction product, or alkylate. The alkylate reaction product generally contains hydrocarbons having seven or more carbon atoms, and it is a highly desirable gasoline blending component because of its high octane value as a motor fuel.

While a process which utilizes a catalyst composition comprising a sulfone component and a hydrogen halide component produces an alkylate product of very high quality, one side effect from using such a process in the production of alkylate is the formation of certain unwanted polymeric reaction by-products such as those referred to as acid-soluble oils, or ASO. These polymeric reaction by-products are referred to as acid-soluble oils; because, they are soluble in the acid catalyst utilized in the alkylation process and, thus, remain in the acid catalyst phase when the alkylate product resulting from the contact of a hydrocarbon mixture with an alkylation catalyst is separated from the alkylation catalyst.

In an alkylation process which continuously separates the catalyst phase from the alkylation reaction product for reuse in the process reaction zone, there is a buildup of ASO and water which accumulates in the catalyst phase. Over time, the ASO and water concentrations will reach unacceptable levels if not removed. A low concentration of ASO or water in the alkylation catalyst comprising a sulfone component and a hydrogen halide component is believed to have a beneficial effect upon the alkylation process or its product. However, higher concentrations in the alkylation catalyst have an adverse effect upon the catalyst activity and the final alkylate end-product. Water and ASO concentrations in the alkylation catalyst that exceed certain acceptable limits will result in lowering the octane of the alkylate end-product with incremental increases in the water or ASO concentration causing incremental decreases in the alkylate octane.

In conventional alkylation processes that use a substantially pure hydrogen fluoride material as a catalyst, as opposed to the use of the aforementioned catalyst mixture comprising a sulfone component and a hydrogen halide component, there are certain known methods for removing the ASO and water from the HF catalyst used in a continuous alkylation process. This is generally done by passing a portion of the HF catalyst to a stripping vessel whereby the HF is stripped from the ASO and water by means of a vaporous hydrocarbon such as isobutane. The bottoms from the stripping vessel in the conventional alkylation process will contain ASO and water removed from the HF catalyst.

In processes that utilize an alkylation catalyst containing both a sulfone component and a hydrogen halide component, the aforementioned means for separating or removing ASO and water from the alkylation catalyst is unsuitable due to the presence of the sulfone. One method for removing water from the alkylation catalyst is to withdraw a vaporous sidedraw stream from the stripping vessel followed by the total condensation of such stream and a liquid-liquid phase separation. While this method seems to provide certain benefits, it still results in a significant loss in HF per volume of water removed with the liquid aqueous phase. It is desirable to minimize the amount of HF that is lost with the liquid aqueous phase.

SUMMARY OF THE INVENTION

It is, therefore, an object of this invention to provide a novel method for removing ASO and water from a sulfone and hydrogen fluoride alkylation catalyst.

A further object of this invention is to provide a method for preventing the accumulation of ASO and water within an alkylation catalyst of a continuous alkylation process.

A still further object of this invention is to provide a method for removing ASO and water from an alkylation catalyst comprising a sulfone, hydrogen halide, ASO and water while minimizing the loss of sulfone with the ASO and water removed from the alkylation catalyst.

A yet further object of this invention is to provide a method for removing water from an alkylation catalyst containing sulfone and HF without the loss of a significant amount of HF along with the removed water.

The present invention is a method for regenerating an alkylation catalyst, containing HF, sulfone, an ASO reaction by-product and water. The alkylation catalyst is regenerated by removing a portion of the ASO reaction by-product and water contained therein while minimizing loss of sulfone with the portion of the ASO reaction by-product and water removed from the alkylation catalyst.

The alkylation catalyst regenerated contains sulfone and HF and has been used in an alkylation process. Particularly, the alkylation process includes the alkylation of an isoparaffin olefin in the presence of the alkylation catalyst within an alkylation reaction zone thereby forming an alkylate product and the ASO reaction by-product. The alkylation reaction zone effluent, containing the alkylation catalyst, the alkylate product, and the ASO reaction by-product, is passed from the alkylation reaction zone to a separation zone for separating the alkylation reaction zone effluent into a hydrocarbon phase, containing the alkylate product, and the alkylation catalyst. A portion of the alkylation catalyst is charged to a stripper which defines a separation zone including an intermediate zone positioned between an upper flash zone and a lower stripping zone. The stripper also provides means for stripping HF from the portion of alkylation catalyst charged thereto and to provide a stripper bottoms stream, stripper sidedraw stream and the stripper overhead stream. An isoparaffin is utilized in the stripper as a stripping gas to provide the stripper overhead stream containing HF, isoparaffin and less than 0.1 weight percent water. The stripper bottom stream contains sulfone and ASO reaction by-product. The stripper sidedraw stream is substantially in the vapor state containing water, HF and isoparaffin. The stripper overhead stream may be combined with the alkylation catalyst and the stripper bottom stream is passed from the stripper. As for the substantially vaporous stripper sidedraw stream, it undergoes partial condensation to thereby form a first liquid, comprising water, and a vapor phase, comprising isoparaffin.

BRIEF DESCRIPTION OF THE DRAWING

The accompanying

Figure 1:
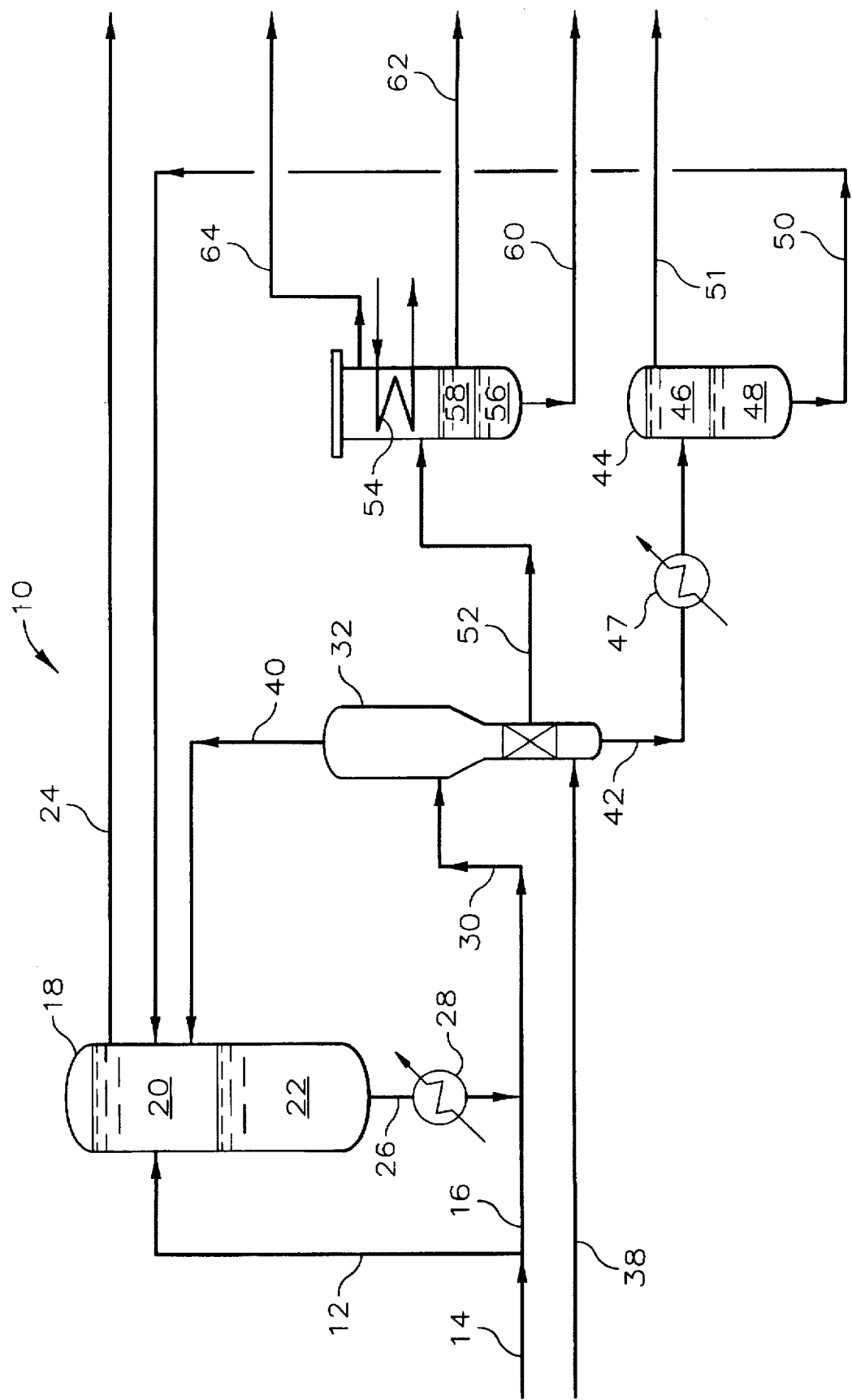
FIG. 1 is a schematic representation of the process which is one embodiment of the invention.

Other objects and advantages of the invention will be apparent from the detailed description of the invention and the appended claims.

DETAILED DESCRIPTION OF THE INVENTION

The acid soluble oil referred to herein is produced as a reaction by-product in an alkylation process comprising the step of contacting a hydrocarbon mixture, which comprises olefins and isoparaffins, with an alkylation catalyst, which comprises a hydrogen halide component and a sulfone component. As used within this description and in the appended claims, the term "acid soluble oil", or "ASO", means those conjunct polymers which are highly olefinic oils produced by acid-catalyzed reactions of hydrocarbons. An extensive description and characterization of certain types of conjunct polymer oils is provided in the *Journal of Chemical and Engineering Data* article entitled "Molecular Structure of Conjunct Polymers", pages 150–160, Volume 8, Number 1, (January 1963) by Miron and Lee. This article is incorporated herein by reference.

The physical properties of ASO depend upon the particular hydrocarbon feed processed, the catalyst utilized in the process, feed contaminants such as hydrogen sulfide, butadiene, oxygenates and other compounds, and the alkylation process reaction conditions. Thus, as the term is more narrowly defined, ASO will be those conjunct polymers produced as a by-product in the catalyzed reaction of mono-olefins with isoparaffins utilizing a catalyst mixture comprising a sulfone component and a hydrogen halide component. The preferred mono-olefins for use in the catalyzed reaction are those having from three to five carbon atoms and the preferred isoparaffins are those having from four to six carbon atoms. The preferred sulfone component is sulfolane and the preferred hydrogen halide component is hydrogen fluoride.

The ASO by-product derived from the hydrocarbon reaction catalyzed by a sulfone-containing alkylation catalyst can be further generally characterized as having a specific gravity, with water at 60° F. as the reference, in the range of from about 0.8 to about 1.0, an average molecular weight in the range of from about 250 to about 350, and a bromine number in the range of from about 40 to about 350. The boiling temperature of the ASO by-product can range from an initial boiling point of about 150° F. to an end-point of about 600° F.

The hydrogen halide component of the alkylation catalyst composition or alkylation catalyst mixture utilized in the alkylation process can be selected from the group of compounds consisting of hydrogen fluoride (HF), hydrogen chloride (HCl), hydrogen bromide (HBr), and mixtures of two or more thereof. The preferred hydrogen halide component, however, is hydrogen fluoride, which can be utilized in the catalyst composition in anhydrous form; but, generally, the hydrogen fluoride component utilized can have a small amount of water.

The sulfones suitable for use in this invention are the sulfones of the general formula

wherein R and R' are monovalent hydrocarbon alkyl or aryl substituents, each containing from 1 to 8 carbon atoms.

Examples of such substituents include dimethylsulfone, di-n-propylsulfone, diphenylsulfone, ethylmethyl-sulfone and the alicyclic sulfones wherein the SO group is bonded to a hydrocarbon ring. In such a case, R and R' are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as, for example, chloromethylethylsulfone. These sulfones may advantageously be used in the form of mixtures.

When sulfolane is used as the preferred sulfone, it can be utilized in the alkylation catalyst composition in anhydrous form, but, more often, the sulfolane component, when added to the alkylation catalyst composition as a make-up component, can have a small amount of water. Generally, the sulfolane component used to form the alkylation catalyst mixture will have a water concentration up to about 5 weight percent of the total weight of the sulfolane and water. However, preferably, the water contained in the sulfolane component will be in the range of from about 0.1 to about 5.0 weight percent of the total weight of the sulfolane and water and, most preferably, the water will be present in the range of from 0.5 to 4 weight percent.

In the alkylation process, the accumulation of water in the alkylation catalyst composition, which comprises hydrogen fluoride and sulfolane, in no event can be more than about 10 weight percent of the total weight of the catalyst composition, which includes sulfone, hydrogen halide and water. Preferably, the concentration of water present in the alkylation catalyst composition is less than about 7.5 weight percent. Most preferably, the concentration of water present in the alkylation catalyst composition is less than 3 weight percent.

Thus, the alkylation catalyst composition used in the alkylation process system wherein an ASO reaction by-product is produced can comprise a hydrogen halide component and a sulfone component, both as described herein, and a concentration of water. Preferably, the ASO by-product will be produced in an alkylation process in which the hydrocarbon mixture is contacted with an alkylation catalyst having sulfolane as its sulfone component and hydrogen fluoride as its hydrogen halide component. In the case where the alkylation catalyst comprises sulfolane and hydrogen fluoride, good alkylation results can be achieved with a weight ratio of hydrogen fluoride to sulfolane in the alkylation catalyst in the range of from about 1:1 to about 40:1. A preferred weight ratio of hydrogen fluoride to sulfolane can range from about 1.2:1 to about 19:1 and, more preferably, it can range from 1.5:1 to 9:1.

In order to improve selectivity of the alkylation reaction of the present invention toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8 to 15. It is emphasized, however, that the above recited ranges for the molar ratio of isoparaffin-to-olefin are those which have been found to be commercially practical operating ranges; but, generally, the greater the isoparaffin-to-olefin ratio in an alkylation reaction, the better the resultant alkylate quality.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 120° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst of the present invention generally should be sufficient to provide for essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40–90 volume percent catalyst phase and about 60–10 volume percent hydrocarbon phase, and wherein good contact of olefin with isoparaffin is maintained in the reaction zone, essentially complete conversion of olefin may be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

In the alkylation process, the reactants can be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. A portion of the catalyst can continuously be regenerated or reactivated as described herein, or by any other suitable treatment, and returned to the alkylation reactor.

To regenerate the alkylation catalyst, a portion of the alkylation catalyst is charged to a stripping vessel for stripping HF from the portion of alkylation catalyst. The stripping vessel defines a separation zone, which includes an intermediate zone positioned between an upper flash zone and a lower stripping zone. As used herein, the term "intermediate zone" is the zone within the stripping vessel which extends from a point immediately above the introduction point of a stripping fluid into the stripping vessel to the bottom of the upper flash zone of such stripping vessel. The stripping vessel, or stripper, provides means for separating the alkylation catalyst into a stripper bottoms stream, a stripper sidedraw stream and a stripper overhead stream by the introduction of a stripping fluid.

The stripper bottoms stream from the stripping vessel contains sulfone, is rich in ASO, and, preferably, contains less than 5 weight percent HF. The stripper overhead stream contains isobutane and HF and further can contain water. However, it is preferred for the stripper overhead stream to be substantially dry having a concentration of water that is less than about 0.1 weight percent and, most preferably, less than 0.05 weight percent.

As for the stripper sidedraw stream, it is drawn from the intermediate zone of the stripping vessel being substantially in the vapor state and containing water, HF and isoparaffin. The vaporous stripper sidedraw stream undergoes a partial condensation resulting in the formation of at least one liquid phase and a vapor phase. It is a necessary and critical aspect of the invention for the vaporous stripper sidedraw stream to be subjected to only a partial, as opposed to a total, condensation. It has been discovered that the partial condensation of the vaporous stripper sidedraw stream allows for the removal of water from the alkylation catalyst with less HF loss than that which occurs when the vaporous stripper sidedraw stream is totally condensed. This reduction in HF loss is the result of the formation of a first liquid phase containing a very high concentration of water. Another second liquid phase can be formed which contains isoparaffin and HF. The vapor phase comprises isoparaffin and, preferably, HF.

The first liquid phase from the partial condensation of the vaporous stripper sidedraw stream comprises water. It is best for the water concentration of the first liquid phase to be maximized. Generally, the water concentration of the vaporous stripper sidedraw stream is in the range of from about 0.05 weight percent to about 1.0 weight percent, but, more commonly, the water concentration can be in the range of from 0.1 weight percent to 0.5 weight percent. The first liquid phase generally can have a water concentration exceeding about 1 weight percent upwardly to about 60 weight percent. But, more commonly, the water concentration of the first liquid phase can be in the range of from about 2 weight percent to about 40 weight percent. Most commonly, the water concentration of the first liquid phase can be in the range of from 4 weight percent to 20 weight percent.

The second liquid phase from the partial condensation of the vaporous stripper sidedraw stream comprises isoparaffin and can further comprise HF. The HF can be present in the second liquid phase upwardly to the solubility limit of HF in the isoparaffin.

The vapor phase from the partial condensation of the vaporous stripper sidedraw stream comprises isoparaffin, and it can further include HF. It is preferred for the vapor phase to be substantially free of water.

The stripper bottoms stream can be passed to a separator for separating ASO and sulfone. One method for performing such separation is to cool the stripper bottoms stream by indirect heat exchange followed by gravitational separation of an ASO phase, comprising ASO, and a sulfone phase, comprising sulfone. The ASO phase is passed from the separator for further processing or disposal, and the sulfone phase may be reused as a portion of the sulfone component of the alkylation catalyst containing sulfone and HF.

Now referring to FIG. 1, there is depicted by schematic representation an alkylation process system 10. A hydrocarbon feed mixture, comprising olefins and isoparaffins, is introduced into riser-reactor 12 through conduit 14. Riser-reactor 12 defines a reaction zone wherein the hydrocarbon feed mixture is contacted, or admixed, with an alkylation catalyst mixture, comprising sulfolane, water, and hydrogen fluoride, in order to produce a reaction product and a reaction by-product. The olefins of the hydrocarbon feed mixture generally comprise one or more olefins having from three to five carbon atoms, and the isoparaffins of the hydrocarbon feed mixture generally will have from four to six carbon atoms. The alkylation catalyst mixture is introduced into riser-reactor 12 via conduit 16.

The admixture of hydrocarbon feed mixture and alkylation catalyst mixture passes through the reaction zone defined by riser-reactor 12 wherein a reaction takes place in which the olefins of the hydrocarbon feed mixture react with isoparaffins of the hydrocarbon feed mixture to produce an alkylate reaction product. Also, within the reaction zone, the alkylation reaction by-product, ASO, is formed.

The reactor effluent, which includes the alkylate product and reaction by-product, from riser-reactor 12 passes to settler vessel 18, which defines a separation zone for separating the alkylate reaction product from the alkylation catalyst mixture to produce a separated reaction product 20 and a separated alkylation catalyst phase 22. The separated alkylation catalyst phase 22 will contain a portion, but, preferably, a substantial portion, of the alkylation reaction by-product, ASO. The separated reaction product 20 passes to downstream processing via conduit 24. The separated alkylation catalyst phase 22 can be recycled via conduits 26 and 16 to riser-reactor 12 for reuse as the alkylation catalyst mixture. Interposed in conduit 26 is catalyst cooler 28, which defines a heat transfer zone for exchanging heat from separated alkylation catalyst phase 22 to a heat transfer fluid such as water.

In order to regenerate the separated alkylation catalyst phase by removing accumulated ASO and water, a portion, sometimes referred to as a slip stream or a drag stream, of the separated alkylation catalyst phase 22 passes by way of conduit 30 to stripping column 32. Stripping column 32 defines a separation zone including an intermediate zone positioned between an upper flash zone and a lower stripping zone and extending from the point of introduction of a stripping fluid to an upper flash zone. Stripping column 32 provides means for stripping HF from the slip stream of alkylation catalyst charged thereto and to provide a stripper bottoms stream, a stripper sidedraw stream and a stripper overhead stream.

The stripping fluid introduced into stripping column 32 by way of conduit 38 is vaporous isobutane which provides energy for separating the slip stream into the stripper overhead stream, stripper sidedraw stream and the stripper bottoms stream and, more specifically, for stripping the hydrogen fluoride from the slip stream. The stripper overhead stream passes from the upper flash zone of stripping column 32 by way of conduit 40 to settler vessel 18. The stripper bottoms stream passes from the lower stripping zone of stripping column 32 by way of conduit 42 to phase separator, or decanter, 44. Interposed in conduit 42 is heat exchanger 47 providing for the cooling by indirect heat exchange of the stripper bottoms stream prior to feeding the cooled stripper bottoms stream to decanter 44. Decanter 44 defines a separation zone and provides for the separation of the cooled stripper bottoms stream into an ASO phase 46 and a sulfone phase 48. The sulfone phase may be recycled to settler vessel 18 through conduit 50. The ASO phase is passed from decanter 44 downstream through conduit 51.

The stripper sidedraw stream passes from the intermediate zone of stripping column 32 by way of conduit 52. The stripper sidedraw stream is substantially in the vapor state containing water, HF and isoparaffin and undergoes a partial condensation induced by condenser 54 to provide a vapor phase, comprising isoparaffin, and at least one liquid phase. Among the liquid phases, a first liquid phase 56, comprising water, and a second liquid phase 58, comprising isoparaffin, are separated. The first liquid phase passes to downstream processing and disposal by way of conduit 60. The second liquid phase, which may also contain HF, can pass downstream for further processing through conduit 62 and the vapor phase can pass downstream through conduit 64. Both the vapor phase and second liquid phase may be recycled, directly or indirectly, to settler vessel 18.

CALCULATED EXAMPLE

This example presents calculated material balance data for the stripper sidedraw condenser when it is operated as a total condenser and when it is operated as a partial condenser of the stripper sidedraw. The data demonstrate the advantage of partial condensation over total condensation of the stripper sidedraw.

TABLE I

| Component | Feed Stream 52 lbs/hr | Vapor Stream 64 lbs/hr | HC Stream 58 lbs/hr | Water Stream 56 lbs/hr |
|---|---|---|---|---|
| Base Case | Totally Condensed Sidedraw (100° F., 130 psia) | | | |
| Propane | 6.53 | 0.00 | 6.52 | 0.01 |
| I-Butane | 162.55 | 0.00 | 162.33 | 0.22 |
| N-Butane | 13.93 | 0.00 | 13.92 | 0.01 |
| C5+ | 1.64 | 0.00 | 1.08 | 0.55 |
| HF | 7.00 | 0.00 | 0.47 | 6.53 |
| Water | 2.30 | 0.00 | 0.00 | 2.30 |
| Total | 193.94 | 0.00 | 184.32 | 9.62 |
| Case 1 | Partially Condensed Sidedraw (200° F., 130 psia) | | | |
| Propane | 9.10 | 9.10 | 0.00 | 0.00 |
| I-Butane | 226.55 | 226.44 | 0.00 | 0.10 |
| N-Butane | 19.41 | 19.41 | 0.00 | 0.00 |
| C5+ | 2.28 | 1.48 | 0.00 | 0.81 |
| HF | 9.76 | 7.30 | 0.00 | 2.46 |
| Water | 3.20 | 0.90 | 0.00 | 2.30 |
| Total | 270.30 | 264.62 | 0.00 | 5.67 |
| Case 2 | Partially Condensed Sidedraw (138° F., 130 psia) | | | |
| Propane | 6.66 | 6.31 | 0.34 | 0.01 |
| 1-Butane | 165.73 | 149.25 | 16.30 | 0.18 |
| N-Butane | 14.20 | 12.44 | 1.75 | 0.01 |
| C5+ | 1.67 | 0.64 | 0.44 | 0.59 |
| HF | 7.13 | 3.57 | 0.03 | 3.53 |
| Water | 2.35 | 0.05 | 0.00 | 2.30 |
| Total | 197.74 | 172.26 | 18.86 | 6.62 |

Table I presents three cases. The base case is a total condensation of the stripper sidedraw in which two separate liquid phases form. The base case shows that when all of the sidedraw is condensed (no vapor phase) the liquid phase containing water shows a higher concentration of HF. This HF is a loss from the system, since the water will be neutralized before disposal.

Both Cases 1 and 2 represent separate conditions for partial condensation of the stripper sidedraw. Case 1 shows that a high temperature partial condensation produces only one liquid phase and it contains less HF for the same amount of water withdrawal (2.3 lbs/hr). Case 2 shows a three phase region exists where there is a vapor phase and two liquid phases. This region exists between about 129° F.–138° F. At the upper end of the temperature range, the water phase contains less HF. Although not as good as in Case 1, it is an improvement over the base case.

As the data of this Example show, the partial condensation of the stripper sidedraw, as opposed to the total condensation, results in a reduction in the amount of HF that is lost with the removed water stream.

While this invention has been described in terms of the presently preferred embodiment, reasonable variations and modifications are possible by those skilled in the art. Such variations and modifications are within the scope of the described invention and the appended claims.

That which is claimed is:

1. A method for regenerating an alkylation catalyst, containing HF, sulfone, an ASO reaction by-product and water, by removing a portion of said ASO reaction by-product and water contained therein while minimizing the loss of sulfone with said portion of said ASO reaction by-product and water removed from said alkylation catalyst, said method comprises the steps of:

alkylating an isoparaffin with an olefin in the presence of said alkylation catalyst within an alkylation reaction zone thereby forming an alkylate product and said ASO reaction by-product;

passing an alkylation reaction zone effluent, containing said alkylation catalyst, said alkylate product, and said ASO reaction by-product, from said alkylation reaction zone to a separation zone for separating said alkylation reaction zone effluent into a hydrocarbon phase, containing said alkylate product, and said alkylation catalyst;

charging a portion of said alkylation catalyst to a stripper which defines a separation zone including an intermediate zone positioned between an upper flash zone and a lower stripping zone, said stripper providing means for stripping HF from said portion of said alkylation catalyst and to provide a stripper bottoms stream, a stripper sidedraw stream and a stripper overhead stream, wherein an isoparaffin is utilized as a stripping gas to provide said stripper overhead stream containing HF, isoparaffin and less than 0.1 weight percent water, said stripper bottoms stream containing sulfone and ASO reaction by-product, and said stripper sidedraw stream is substantially in the vapor state containing water, HF and isoparaffin;

adding said stripper overhead stream to said alkylation catalyst in said separation zone;

passing said stripper bottoms stream from said stripper; and partially condensing said stripper sidedraw stream thereby forming a first liquid phase, comprising water, and a vapor phase, comprising isoparaffin.

2. A method as recited in claim 1 wherein the concentration of water in said first liquid phase exceeds about 1 weight percent upwardly to about 60 weight percent.

3. A method as recited in claim 2 further forming a second liquid phase comprising isoparaffin.

4. A method as recited in claim 3 wherein said first liquid phase further comprises HF.

5. A method as recited in claim 4 wherein said second liquid phase further comprises HF.

6. A method as recited in claim 5 wherein said vapor phase further comprises HF.

* * * * *